USO10549037B2

(12) United States Patent
Estes (10) Patent No.: US 10,549,037 B2
(45) Date of Patent: *Feb. 4, 2020

(54) GLUCAGON ADMINISTRATION SYSTEM AND METHODS (71) Applicant: Bigfoot Biomedical, Inc., Milpitas, CA (US)

(72) Inventor: Mark C. Estes, Malibu, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 115 days.

This patent is subject to a terminal disclaimer.

(21) Appl. No.: 15/462,334

(22) Filed: Mar. 17, 2017

(65) Prior Publication Data

US 2017/0189615 A1    Jul. 6, 2017

Related U.S. Application Data (63) Continuation of application No. 14/320,863, filed on Jul. 1, 2014, now Pat. No. 9,629,901.

(51) Int. Cl.
*A61M 5/172* (2006.01)
*A61K 38/26* (2006.01)
(Continued)

(52) U.S. Cl.
CPC .......... *A61M 5/1723* (2013.01); *A61K 38/26* (2013.01); *A61M 5/003* (2013.01); *A61M 5/14244* (2013.01); *A61M 5/14248* (2013.01); *A61M 5/24* (2013.01); *A61M 2202/0486* (2013.01); *A61M 2205/3561* (2013.01);
(Continued)

(58) Field of Classification Search
CPC .......... A61M 5/1723; A61M 2230/201; A61M 2005/14208; A61M 2205/3592; A61M 2205/50; A61M 2205/52; A61M 2230/005
See application file for complete search history.

(56) References Cited

U.S. PATENT DOCUMENTS 5,984,894 A    11/1999 Poulsen
6,126,595 A    10/2000 Amano et al.
(Continued)

FOREIGN PATENT DOCUMENTS

CA    2543545    5/2005
DE    196 27 619 A    1/1998
(Continued)

OTHER PUBLICATIONS

"Using the Deltec Cozmo Insulin Pump Correction Bolus Feature" believed to be publicly available before May 5, 2008, pp. 36-41.
(Continued)

*Primary Examiner* — Emily L Schmidt
(74) *Attorney, Agent, or Firm* — Fish & Richardson P.C.

(57) ABSTRACT

Some embodiments a glucagon administration system can provide a suggested glucagon dosage based on one or more particular parameters (e.g., the user's recent blood glucose characteristics, a glucagon sensitivity value of the user, and other parameters). In some circumstances, the glucagon administration system can receive information indicative of the user's blood glucose level and suggest a glucagon dosage that is at least partially dependent upon a previously stored glucagon sensitivity for the user.

10 Claims, 4 Drawing Sheets (51) Int. Cl.
*A61M 5/00* (2006.01)
*A61M 5/24* (2006.01)
*A61M 5/142* (2006.01)

(52) U.S. Cl.
CPC .............. *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/8206* (2013.01); *A61M 2230/201* (2013.01)

(56) References Cited

U.S. PATENT DOCUMENTS

| | | |
|---|---|---|
| 6,233,471 B1 | 5/2001 | Berner et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B2 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga |
| 6,659,980 B2 | 12/2003 | Moberg et al. |
| 6,663,602 B2 | 12/2003 | Moller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,925,393 B1 | 8/2005 | Kalatz et al. |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,104,972 B2 | 9/2006 | Moller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,278,983 B2 | 10/2007 | Ireland et al. |
| 7,291,107 B2 | 11/2007 | Hellwig et al. |
| 7,879,026 B2 | 2/2011 | Estes et al. |
| 8,105,268 B2 | 1/2012 | Lebel et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0167464 A1 | 8/2004 | Ireland et al. |
| 2004/0171983 A1 | 9/2004 | Sparks et al. |
| 2004/0176720 A1 | 9/2004 | Kipfer |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |

(56) References Cited

U.S. PATENT DOCUMENTS

| | | |
|---|---|---|
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Estes |
| 2005/0222645 A1 | 10/2005 | Malave et al. |
| 2005/0238507 A1 | 10/2005 | Ditanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0173406 A1 | 8/2006 | Hayes et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0088271 A1 | 4/2007 | Richards |
| 2007/0118405 A1 | 5/2007 | Campbell et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173761 A1 | 7/2007 | Kanderian, Jr. et al. |
| 2007/0179444 A1 | 8/2007 | Causey et al. |
| 2008/0125700 A1 | 5/2008 | Moberg et al. |
| 2008/0172027 A1 | 7/2008 | Blomquist |
| 2008/0177165 A1 | 7/2008 | Blomquist et al. |
| 2008/0294094 A1 | 11/2008 | Mhatre et al. |
| 2008/0294142 A1 | 11/2008 | Patel et al. |
| 2008/0306434 A1 | 12/2008 | Dobbles et al. |
| 2008/0306444 A1 | 12/2008 | Brister |
| 2010/0174266 A1 | 7/2010 | Estes |
| 2011/0313390 A1* | 12/2011 | Roy .................. A61M 5/158 604/500 |
| 2012/0123234 A1 | 5/2012 | Atlas et al. |
| 2012/0289931 A1 | 11/2012 | Robinson et al. |
| 2016/0331898 A1* | 11/2016 | Damiano ............. G16H 15/00 |

FOREIGN PATENT DOCUMENTS

| | | |
|---|---|---|
| DE | 102 36 669 | 2/2004 |
| DE | 20 2005 012 358 | 10/2005 |
| EP | 0 062 974 | 10/1982 |
| EP | 0 098 592 | 1/1984 |
| EP | 0 275 213 | 7/1988 |
| EP | 0 496 141 | 7/1992 |
| EP | 0 612 004 | 8/1994 |
| EP | 0 580 723 | 10/1995 |
| EP | 1 045 146 | 12/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| WO | WO 1990/015928 | 12/1990 |
| WO | WO 1997/021457 | 6/1997 |
| WO | WO 1998/011927 | 3/1998 |
| WO | WO 1998/057683 | 12/1998 |
| WO | WO 1999/021596 | 5/1999 |
| WO | WO 1999/039118 | 8/1999 |
| WO | WO 1999/048546 | 9/1999 |
| WO | WO 2001/072360 | 10/2001 |
| WO | WO 2001/091822 | 12/2001 |
| WO | WO 2001/091833 | 12/2001 |
| WO | WO 2002/040083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |
| WO | WO 2010/097796 | 9/2010 |

OTHER PUBLICATIONS

"Which Insulin Pump is Right for Me?", Albany Medical Center, Goodman Diabetes Service, Jan. 2006, 4 pages.
Asante Pearl, Insulin Pump User Manual, 2012, 180 pages.
Collins and Lee, "Microfluidic flow transducer based on the measurement of electrical admittance," *Lab Chip*, 2003, 12 pages.
Debiotech News Release, "Debiotech reveals its new miniaturized Disposable Insulin Nanopump™ for Diabetes therapy," available at http://www.debiotech.com/news/nw_159.html Apr. 24, 2006, 3 pages.
European Patent Office, International Search Report & Written Opinion for Application No. PCT/US2009/069937, dated May 27, 2010, 18 pages.
Medtronic News Release, "Medtronic Receives FDA Approval for World's First Insulin Pump with Real-time Continuous Glucose Monitoring," Apr. 13, 2006, 3 pages.
Patent Abstracts of Japan, vol. 1999, No. 04, and JP 11 010036 , Apr. 30, 1999 and Jan. 19, 1999, Toray Ind. Inc., 6 pages.
Walsh et al., "Guidelines for Insulin Dosing in Continuous Subcutaneious Insulin Infusion Using New Formulas from a Retrospective Study of Individuals with Optimal Glucose Levels", *J. Diabetes Science and Technology*, Sep. 2010, 4(5):8 pages.
Walsh et al.,"Guidelines for Optimal Bolus Calculator Settings in Adults", *J. Diabetes Science and Technology*, Jan. 2011, 5(1):7 pages.
International Search Report and Written Opinion in International Application No. PCT/US2015/38843, 11 pages.

\* cited by examiner

GLUCAGON ADMINISTRATION SYSTEM AND METHODS

CROSS-REFERENCE TO RELATED APPLICATIONS

This application is a continuation application of and claims priority to U.S. application Ser. No. 14/320,863, filed on Jul. 1, 2014.

TECHNICAL FIELD

This disclosure relates to systems and methods for delivery of medicinal fluids, such as infusion pump systems for the delivery of glucagon, insulin, or both, other delivery devices (such as glucagon "pens"), or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin into the subcutaneous tissue and to the vasculature of diabetes patients so as to regulate blood-glucose levels. In some circumstances, the dosage of medicine delivered by the infusion pump can be calculated by the infusion pump system. In these circumstances, the infusion pump system can take into account many variables, including user input, when making such calculations.

Other forms of fluid delivery to a targeted individual are also possible. For example, insulin, glucagon, or another medicine can be injected using a manual syringe or a single use injection "pen." In some circumstances, an injectable form of glucagon is used in emergency aid of severe hypoglycemia when the victim is unconscious or for other reasons cannot take glucose orally. The glucagon fluid can be rapidly injected to the patient by intramuscular, intravenous or subcutaneous injection, and quickly raises the blood glucose level of the patient.

SUMMARY

Some embodiments a glucagon administration system can provide a suggested glucagon dosage based on one or more particular parameters (e.g., the user's recent blood glucose characteristics, food intake data, an amount of insulin already delivered to the user which has not yet acted on the user, glucagon sensitivity of the user, and the like). In some circumstances, a controller device of the glucagon administration system can receive information indicative of the user's blood glucose level and suggest a glucagon dosage that is at least partially dependent upon a stored glucagon sensitivity value that is predetermined for the user. Such a glucagon dosage suggestion feature can be initiated, for example, by the glucagon administration system in response to input of a blood glucose level that is below a target level, or in response to a combination of the blood glucose level, previously delivered insulin dosages, and a user's insulin sensitivity value that permit the system to predict a pending low glucose event. Accordingly, the suggested glucagon dosage can vary depending on one or more of these parameters. Such a feature can be helpful to a user when a glucagon administration device is operated in conjunction with a glucose monitoring device (or an insulin pump that receives data of blood glucose levels) because the suggested glucagon dosage can be at least partially based on recent data indicative of the user's blood glucose level (and, optionally, recent insulin use).

Particular embodiments described herein may include a glucagon administration system. The system may include a portable pump housing that receives a medicinal fluid for dispensation to a user. The pump housing may at least partially contain a pump drive system to dispense the medicinal fluid through a flow path to the user. The system may also include a controller that communicates with the pump drive system to dispense the medicinal fluid from the portable pump housing. The controller may be configured to activate a glucagon dosage calculator that calculates a suggested glucagon dosage value based at least in part on a glucagon sensitivity parameter, which can be, optionally, stored in a computer-readable memory device of the controller.

Some embodiments described herein include a method of operating glucagon administration system. The method may include receiving, by a controller of an infusion pump system, glucose information indicative of a blood glucose level of a user. The method may also include detecting, by the controller of an infusion pump system, that the blood glucose level of the user is less than a threshold value stored by the controller of the infusion pump system. The method may further include activating a glucagon dosage calculator configured to determine a suggested glucagon dosage according to a function that is at least partially dependent upon (i) a glucagon sensitivity parameter stored by the controller of the infusion pump system, (ii) the blood glucose level of the user, and (iii) a targeted blood glucose level of the user. The method may optionally include displaying on a display screen the suggested glucagon dosage, the blood glucose level of the user, and an indication that the rate of change in the blood glucose level in increasing or decreasing.

Additional embodiments described herein include a method of determining a suggested glucagon dosage. The method may include storing, at a portable computing system, a parameter value indicative of a glucagon sensitivity of a user. The method may also include receiving, by the portable computing system, glucose information indicative of a blood glucose level of the user. The method may further include comparing, by the portable computing system, the blood glucose level of the user to threshold level to determine that the blood glucose level of the user is below the threshold level. The may include calculating a suggested glucagon dosage for the user using at least the parameter value indicative of the glucagon sensitivity of the user. Optionally, this calculating operation may be in response to determining that the blood glucose level of the user is below the threshold level. The method may also include displaying on a display screen the suggested glucagon dosage.

In some embodiments described herein, a medicine administration system includes pump device (which may optionally be disposable and non-reusable) and a removable controller device. The pump device may include a pump housing that defines a space to receive an insulin cartridge. The pump device may also include a drive system to dispense insulin when the insulin cartridge is received by the pump housing. The drive system may include a piston rod that is incrementally movable to apply a dispensing force. The removable controller device may include a controller housing that is removably attachable to the pump housing in a fixed relationship to provide an electrical connection between the controller device and the pump device. The removable controller device may include control circuitry arranged in the controller housing to electrically communicate with the drive system in the pump housing. Also, the removable controller device may include a user interface connected to the control circuitry, the user interface including a display and one or more user-selectable buttons. The removable controller device may further include a wireless communication device to receive glucose information from a wearable monitoring device. The glucose information may be indicative of a blood glucose level of the user. The removable controller device may displays a suggested glucagon dosage (which may optionally occur in response to user input to the user interface). The suggested glucagon dosage may be at least partially dependent upon a glucose sensitivity value stored by the controller device, a target blood glucose level stored by the controller device, and the blood glucose level of the user.

These and other embodiments described herein may provide one or more of the following advantages. First, some embodiments of a glucagon administration system can implement a glucagon dosage calculator, which is configured to accurately calculate a suggested glucagon bolus dosage based upon the user's glucagon sensitivity value (stored by a controller) and other parameters (e.g., the user's target blood glucose level, the users current blood glucose level, the rate of change of the user's blood glucose level, the user's recent or pending food intake, the user's previously dosed insulin that has not yet acted (an insulin-on-board value, a total insulin load, value, or the like), the user's activity level, or a combination thereof). The user's glucagon sensitivity value, which may be a personalized parameter indicative of the user's bodily response to glucagon, can be manually input by a clinician or by the user or can be calculated by the controller based upon the user's historical treatment data.

Second, in some embodiments of the systems described herein, the user's glucagon sensitivity value can be stored in a computer-readable memory of the system and accessed by the controller device when the glucagon dosage calculator is activated. When the suggested glucagon dosage value is calculated, the system can display the suggested glucagon dosage to the user such that the user can make an informed decision regarding glucagon delivery. In some embodiments, the user can readily accept the suggested glucagon dosage by pressing a single button on the user interface, which then prompts a glucagon pump device to dispense the dosage to the user via an infusion set or other fluid delivery path to the user. In alternative embodiments, the user can view the displayed suggestion for the glucagon dosage value and then manually inject the suggested dosage using a glucagon injector pen device.

Third, the system may utilize this glucagon bolus calculation feature in combination with a glucose monitoring device that continuously transmits blood glucose information (e.g., every minute, every two minutes, every five minutes, every ten minutes, or the like) to the controller. The blood glucose information from the glucose monitoring device can be used by the glucagon administration system to determine the user's recent blood glucose value, the recent rate of change in the user's blood glucose level, or both. The glucagon calculator feature of the system can use such glucose level/rate-of-change parameter to accurately calculate a suggested glucagon dosage as described in more detail below.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
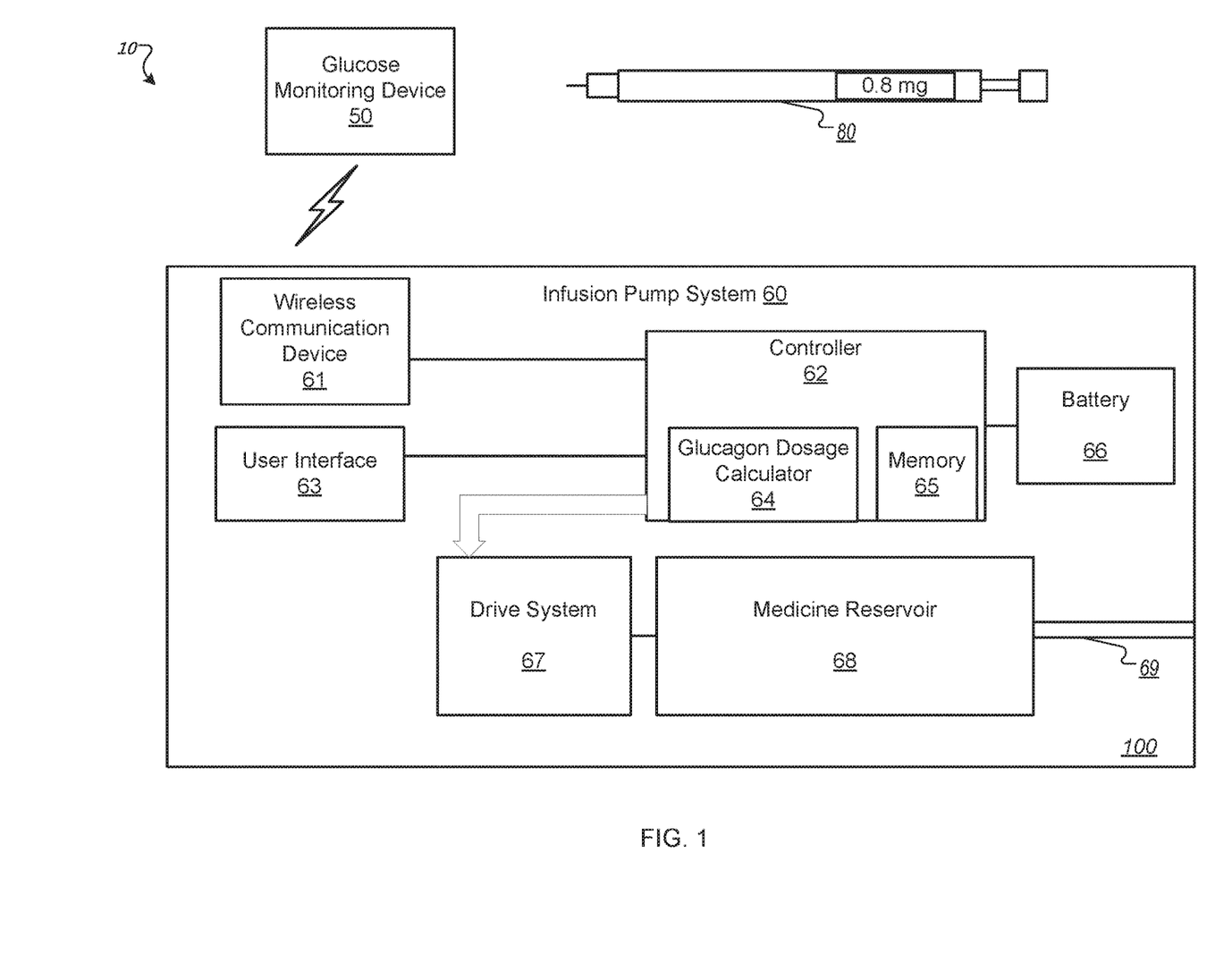
FIG. 1 is a block diagram of an infusion pump system in accordance with some embodiments.

Referring to FIG. 1, a medicine administration system 10 can include an infusion pump system 60 configured to controllably dispense dosages of glucagon, insulin, or both. For example, the infusion pump system 60 can be used to deliver glucagon, insulin, or another medicinal fluid for purposes of regulating the user's blood glucose (BG) levels. In some optional embodiments, the medicine administration system 10 may include a glucose monitoring device 50 that communicates with a wireless communication device 61 of the infusion pump system 60 so as to supplying data indicative of a user's blood glucose level to a controller 62 included in the infusion pump system 60. Alternatively or additionally, the data indicative of a user's blood glucose level can be manually input to the controller 62 via a user interface 63 of the infusion pump system 60. The infusion pump system 60 can utilize the data indicative of a user's blood glucose level in the calculation of a suggested glucagon dosage, which can be accomplished using a glucagon dosage calculator 64 implemented by the controller 62 of the infusion pump system 60.

Briefly, in this embodiment, the infusion pump system 60 is configured to accurately calculate a suggested glucagon bolus dosage based upon the user's glucagon sensitivity value (stored by a memory device 65 of the controller 62) and other parameters (e.g., the user's target blood glucose level, the users current blood glucose level, the rate of change of the user's blood glucose level, the user's recent or pending food intake, the user's previously dosed insulin that has not yet acted (an insulin-on-board value, a total insulin load, value, or the like), the user's activity level, or a combination thereof). The user's glucagon sensitivity value, which may be a personalized parameter indicative of the user's bodily response to glucagon, can be manually input by a clinician or by the user or can be calculated by the controller 62 based upon the user's historical treatment data. When the suggested glucagon dosage value is calculated, the suggested glucagon dosage can be displayed to the user (e.g., refer to FIG. 2 in one embodiment) such that the user can make an informed decision regarding glucagon delivery.

Still referring to FIG. 1, the infusion pump system 60 includes at least one battery 66 configured to provide electrical power to the controller 62. The controller 62 is configured to control the administration of glucagon or another medication to the user by sending control signals to drive system 67, which includes a battery-powered actuator (such as a rotational motor) in this embodiment. For example, the user can input via the user interface 63 a dosage level of glucagon to administer from the infusion pump system 60. The controller can use the received input to generate control signals that are transmitted to the drive system 67 to cause the battery-powered actuator to activate and thereby urge the selected amount of glucagon from the glucagon reservoir 68, which may be a pre-filled cartridge slidably received within the housing of the pump system 60. In such embodiments, the drive system 67 can advance a plunger into the cartridge 68 so as to dispense glucagon therefrom, which causes the glucagon to be dispensed through tubing 69 of an infusion set. It should be understood from the description herein that, in some embodiments, the pump system can be configured to receive two or more medicine cartridges (e.g., the cartridge 68 containing glucagon and a second cartridge (not shown in FIG. 1) for dispensing insulin or another medication) that are controlled by the drive system 67. Alternatively, in other embodiments, the reservoir 68 can contain insulin that is controllably dispensed by the drive system 67 but the glucagon dosage calculator 64 can still be implemented so that the user can view the suggested glucagon dosage value and manually apply the glucagon dosage using a separate device of the administration system 10 (e.g., a glucagon injector 80).

As described in more detail below, the medicine cartridge 68 can be received within a cavity in the infusion pump system 60. In some embodiments, the cartridge 68 is a replaceable cartridge such that, when the replaceable cartridge is exhausted, the replaceable cartridge can be removed from the infusion pump system 60 and replaced with another new pre-filled cartridge. In other embodiments (refer to FIG. 2 below), the cartridge 68 may be non-removably received in the pump system such that, when the glucagon cartridge 68 is exhausted, the portion of the pump system 60 that retains cartridge 68 is discarded along with the cartridge 68 (refer, for example, to FIG. 2). For example, as described in more detail below, the infusion pump system 60 may optionally comprise multiple readily detachable portions, with various components of the infusion pump 100 residing in different detachable portions. In one example described in FIG. 2 below, at least the controller 62, the user interface 63, and the wireless communication device 61 can be contained within a first (reusable) detachable portion while the battery 66, the drive system 67, and the glucagon cartridge 68 are contained within a second (disposable, single-use) detachable portion.

Still referring to FIG. 1, in some implementations, the controller 62 is configured to determine a suggested glucagon dosage for a medication based on various parameters associated with the user. As previously described, the controller 62 can cause the suggested dosage to be displayed on the user interface 63 of the infusion pump system 60, or on a display in communication with the infusion pump system 60. In some implementations, the infusion pump system 60 can include wired or wireless communication capabilities (e.g., via a data cable or via the wireless communication device 61) to allow the controller 62 to transmit the recommended dosage to another device. For example, the controller 62 can calculate a recommended glucagon dosage and use the wireless communication device 61 to transmit (via Bluetooth connectivity or another short-range wireless connection) the recommended glucagon dosage to a user's mobile phone for display to the user.

In particular embodiments, the controller 62 can be configured to determine a suggested glucagon dosage to administer to a user to maintain or return the user's blood glucose level to a targeted value within a predetermined range. For example, the infusion pump system 60 can receive information indicative of the user's blood glucose level, either through wireless communication of a blood glucose level of the user from the glucose monitoring device 50, from a blood glucose meter (e.g., a blood test strip reader) in wireless communication with the infusion pump system 60, or by receiving manual data input via the user interface 63 indicating a blood glucose level of the user. If the blood glucose level is below a predetermined blood glucose threshold level or otherwise below a predetermined safety range for the blood glucose level, or if the rate of change of the user's blood glucose level indicates that the user's blood glucose level will fall below the predetermined safety range within the near future, the controller 62 can activate the glucagon dosage calculator 64 so as to determine a suggested glucagon dosage to return the user's blood glucose level to the desired range.

As described in more detail below, the controller 62 can be configured to access a number of parameters (some or all of which are stored and updated in the memory device 65) when determining a suggested glucagon dosage. These parameters can include glucagon sensitivity of the user, current blood glucose level of the user, target blood glucose level(s), food intake by the user, previous insulin doses, previous glucagon doses, and activity level of the user. The glucagon sensitivity of the user can be a patient-specific value or time-of-day dependent series of values, that is indicative how a particular user reacts to administration of glucagon. In some embodiments, the stored glucagon sensitivity value represents a user-specific value that correlates the number of units (e.g., mg or mcg) of glucagon required to alter the user's blood glucose level by 1 mg/dL, or inversely how many mg/dL of glucose change will be achieved by a standardized dosage unit of glucagon. For example, in this embodiment, the stored glucagon sensitivity value represents a user-specific value that correlates the number of units (e.g., mg or mcg) of glucagon required to alter the user's blood glucose level by 1 mg/dL. Food intake data can include information on the amount of carbohydrates, fats, proteins, or other nutrients recently ingested by the user (or, in some embodiments, soon to be ingested by the user). Information on a user's insulin load can be used in determining a recommended glucagon dosage and can include an estimated value of previously dispensed insulin that has not yet acted in the user's body, such as total insulin load (TIL) information (e.g., an insulin load calculation that includes previous basal and bolus dosages, previously consumed food, or the like), traditional insulin-on-board estimates (which typically account for only bolus dosages), or other such estimated insulin load values. Activity level can be a user-specific, time-sensitive value represented by a time based decay function that assumes activity has a near term effect of significantly lowering glucose within an hour or less of the activity as well as a long term effect of lowering glucose to a lesser degree over a period of 4 to 8 hours. Such an activity level can be detected by the sensors of the pump system 60 (e.g., a set of accelerometers housed within the pump system 60) or manually input via the user interface 63.

Optionally, when the suggested glucagon dosage is calculated by the pump system 60, the controller 62 can display the suggested glucagon dosage to the user along with a prompt for the user to accept or reject the dosage amount for dispensation. For example, the controller 62 can cause the user interface 63 to display the suggested glucagon dosage and prompt the user to accept or reject the recommended dosage. If the user accepts the recommended dosage, the controller 62 can generate control signals to cause the drive system 67 to dispense the suggested dosage of glucagon from the glucagon cartridge 68.

Alternatively, in some embodiments in which the reservoir 68 is exhausted or contains a medicinal fluid other than glucagon (e.g., insulin), the controller 62 can still use the glucagon dosage calculator 64 provide the suggested glucagon dosage to the user to allow the user to administer the suggested dosage using a separate glucagon injector 80 or another glucagon dispensing device external from the pump system 60. For example, the infusion pump system 60 may be an infusion pump for dispensing insulin and the cartridge 68 can contain insulin for dispensing in response to control signals generated by the controller 62 for controlling the drive system 67. The controller 62 can execute the glucagon dosage calculator 64 to provide a suggested glucagon dosage to the user (e.g., by displaying the suggested dosage on a display screen of the user interface 63, or by wirelessly transmitting (via the device 61) the suggested glucagon dosage value for display on another device, such as a personal computer, mobile phone, tablet device, or glucagon pump or pen injector device). The user can then manually administer the suggested glucagon dosage using the glucagon injector 80 (e.g., a glucagon pen or a syringe device) or another glucagon delivery device external from the infusion pump system 60.

In some implementations, the glucagon dosage calculator 64 is implemented by a device other than an infusion pump system 60. For example, such suggested glucagon dosage determinations can be made implemented by a glucagon dosage calculator implemented as a computer-readable program executed on a smart phone or tablet device, by control circuitry of a blood glucose meter, or by a glucagon dosage suggestion calculator attached to or configured to interact with a glucagon delivery device such as a glucagon pen injector 80.

Figure 2:
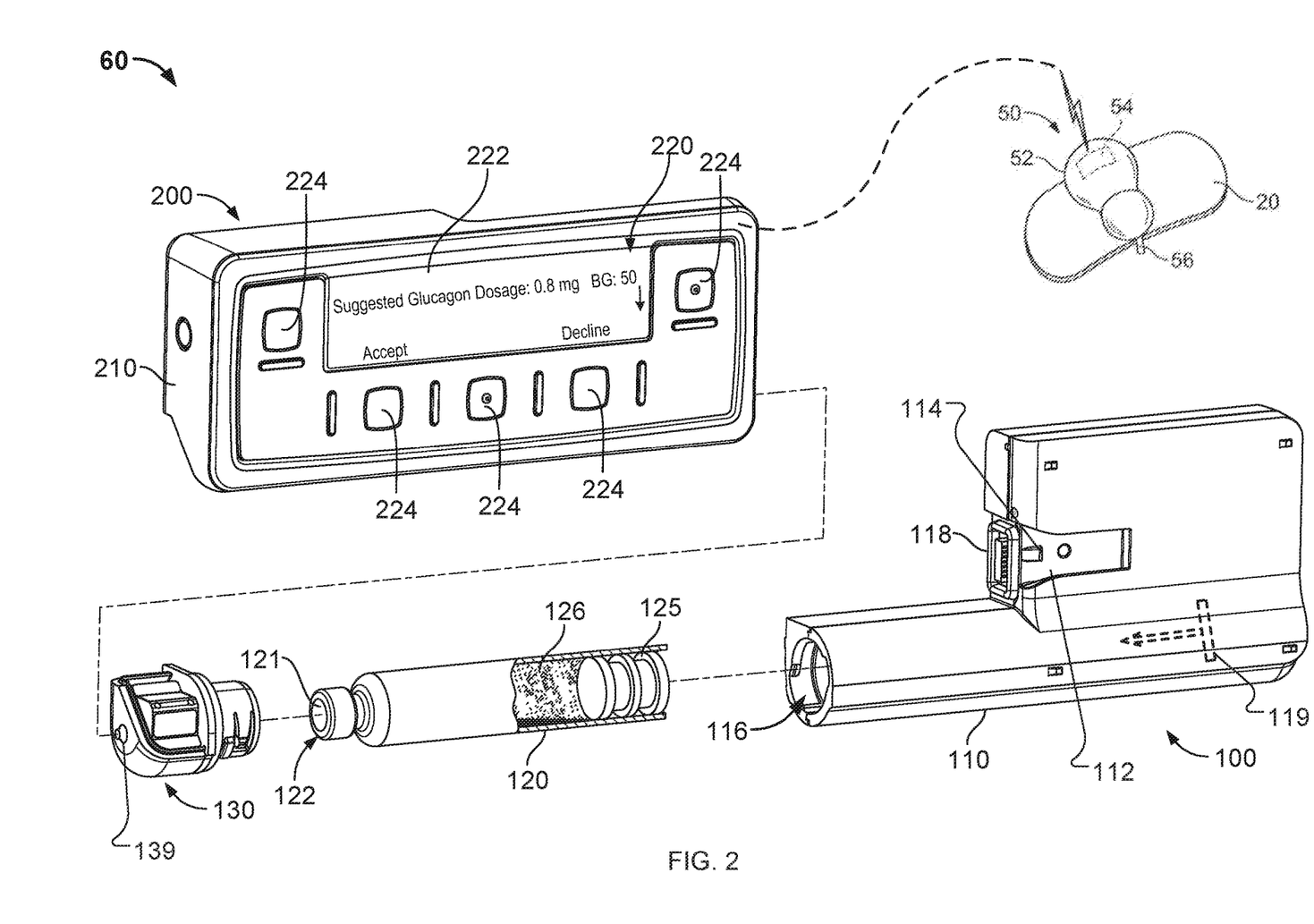
FIG. 2 is a perspective exploded view of an infusion pump assembly in accordance with some embodiments.

Referring now to FIG. 2, an infusion pump system 60 can include a pump device 100 and a removably attachable controller device 200 that are used together for purposes of supplying insulin, glucagon, or another medication to a user. In some embodiments, the infusion pump system 60 may include a glucose monitoring device 50 that communicates with the controller device 200 for the purpose of supplying data indicative of a user's blood glucose level to the controller device 200 of the pump system 60. Similar to the previously described controller 62 (FIG. 1), the controller device 200 in this embodiment can utilize the data indicative of a user's blood glucose level in the calculation of a suggested glucagon dosage. For example, the controller device 200 can detect when the user's current blood is below a target level or a predetermined safety range. In response thereto, the controller device 200 can implement the glucagon dosage calculator (previously described) calculate a suggested glucagon dosage for the user to return the user to the target blood glucose range. As another example, the controller device 200 can calculate the recent rate of change in the user's blood glucose level and can use this rate-of-change information as a parameter in the calculation of a suggested glucagon dosage for the user.

In some embodiments, the pump system 60 can be configured to supply scheduled basal dosages of insulin (or glucagon or another medication) along with user-selected bolus dosages. For example, the pump device 100 is configured to receive a preloaded cartridge 120 of a medicinal liquid, such as insulin or glucagon, which is then controllably dispensed to the user.

As previously described, even in the embodiments in which the pump system 60 dispenses insulin from the cartridge 120 (FIG. 2), the controller device 200 can still implement the glucagon dosage calculator 64 (FIG. 1) so that the user can view the suggested glucagon dosage value and manually apply the glucagon dosage using a separate device of the administration system (e.g., the glucagon injector 80 or another glucagon delivery device). In such embodiments, the insulin basal delivery rate can be selected to maintain a user's blood glucose level in a targeted range during normal activity when the user is not consuming food items. The user-selected bolus deliveries of insulin may provide substantially larger amounts of insulin in particular circumstances, such as when the user consumes food items, when the user's blood glucose level increases beyond a safe limit, when the user's blood glucose level rises faster than a threshold rate, or other scenarios in which the blood glucose level requires a significant correction.

In some alternative embodiments, the pump system 60 can be configured to supply dosages of glucagon to the user. For example, the glucagon dosages can be user selected, or administered in response to user input prompted by a suggested glucagon dosage provided by the pump system 60.

Still referring to FIG. 2, the pump system 60 can be configured to execute the glucagon dosage calculator 64 (FIG. 1) in any of these various embodiments (in the embodiments in which the pump system 60 dispenses insulin from the cartridge 120 (and glucagon from the glucagon injector 80 or another glucagon delivery device), in embodiments in which the pump system 60 dispenses glucagon from the cartridge 120, or other embodiments described herein). For example, a recommendation to administer glucagon, along with a suggested glucagon dosage amount can be provided by the pump system 60 when the user's blood glucose level decreases beyond a safe limit, when the user's blood glucose level falls faster than a threshold rate, or other scenarios in which the blood glucose level requires a significant correction to avoid projected low glucose levels. In some embodiments, the pump system 60 may modify a suggested glucagon dosage in response to certain circumstances. For example, the pump system 60 may increase a suggested glucagon dosage based on a rapidly falling blood glucose level, a current blood glucose level that is below a threshold limit, a detection of a high level of physical activity, or the like.

As described in more detail below, the controller device 200 can suggest a glucagon dosage to the user based, at least in part, on the user's "insulin load." As described herein, "insulin load" includes an estimated value of previously dispensed insulin that has not yet acted in the user's body, such as total insulin load (TIL) information (e.g., an insulin load calculation that includes previous basal and bolus dosages, previously consumed food, or the like), traditional insulin-on-board estimates (which typically account for only bolus dosages), or other such estimated insulin load values. Due in part to pharmacokinetic effects (e.g., the time it takes for insulin to enter the blood stream from the subcutaneous point of delivery) and pharmacodynamic effects (e.g., the time it takes for a concentration of insulin in the blood to have the physiological effect of lower blood glucose level), basal and bolus insulin dispensed into the user's system may not act instantaneously, but instead may act over a period of time to control the user's blood glucose level. As such, the user's body may include some amount of insulin that has not yet acted even while the infusion pump system 60 is activated to deliver additional dosages (basal, bolus, or a combination thereof). In these circumstances, the infusion pump system 60 can be used to determine a user's insulin load, which can provide an estimate of the insulin which was delivered but has not yet acted in the user's body. This insulin load information can be used as a parameter in the calculation of the suggested glucagon dosage.

The controller device 200 can also access a glucagon sensitivity value stored in an internally housed memory device of the controller device 200, and the glucagon sensitivity value can serve as a patient-specific parameter for determining a suggested glucagon dosage for the user. Glucagon sensitivity represents a user specific value that correlates the number of units of glucagon (e.g., mg or mcg) required to alter the user's blood glucose level by 1 mg/dL. The glucagon calculator executed by the controller device 200 can use this user-specific value to determine how much glucagon to administer to the user to reach a target blood glucose level for the user, when the current blood glucose level of the user is below the target value.

In some embodiments, the controller device 200 can suggest a glucagon dosage to the user in a manner that accounts for the user's food intake, the user's blood glucose information (including the rate of change in the blood glucose level), previously delivered insulin that has not yet acted on the user, and previously delivered glucagon that has not yet acted on the user. As described in more detail below, this process for determining a suggested glucagon dosage can accurately reflect food intake data entered into the controller device 200 by the user, the user's recent blood glucose level (e.g., input into the controller device 200 by the user, transmitted to the controller device 200 from the blood glucose monitoring device 50, transmitted from an external blood glucose meter, or the like), the recent rate of change in the user's blood glucose level, and the user's insulin load. For example, a user can enter information indicative of a user activity (e.g., a 6 mile run that will start in 15 minutes, a 6 mile run that started 50 minutes ago, or the like) into the controller device 200, and use the entered information in determining a suggested glucagon dosage for returning the user's blood glucose level to a desired value. The user can benefit from a glucagon dosage determination system that also takes into account other parameters so that a more accurate glucagon dosage can be suggested. For example, the controller device 200 can be configured to provide a more accurate glucagon dosage suggestion by accounting for the user's blood glucose level, the rate of change in the user's blood glucose level, and/or the user's glucagon sensitivity.

Still referring to FIG. 2, the glucose monitoring device 50 can include a housing 52, a wireless communication device 54, and a sensor element 56. The wireless communication device 54 can be contained within the housing 52 and the sensor shaft 56 can extend outward from the housing 52. In use, the sensor element 56 can penetrate the skin 20 of a user to make measurements indicative of characteristics of the user's blood (e.g., the user's blood glucose level or the like). In response to the measurements made by the sensor element 56, the glucose monitoring device 50 can employ the wireless communication device 54 to transmit data to the controller device 200 of the pump assembly 60.

Figure 3:
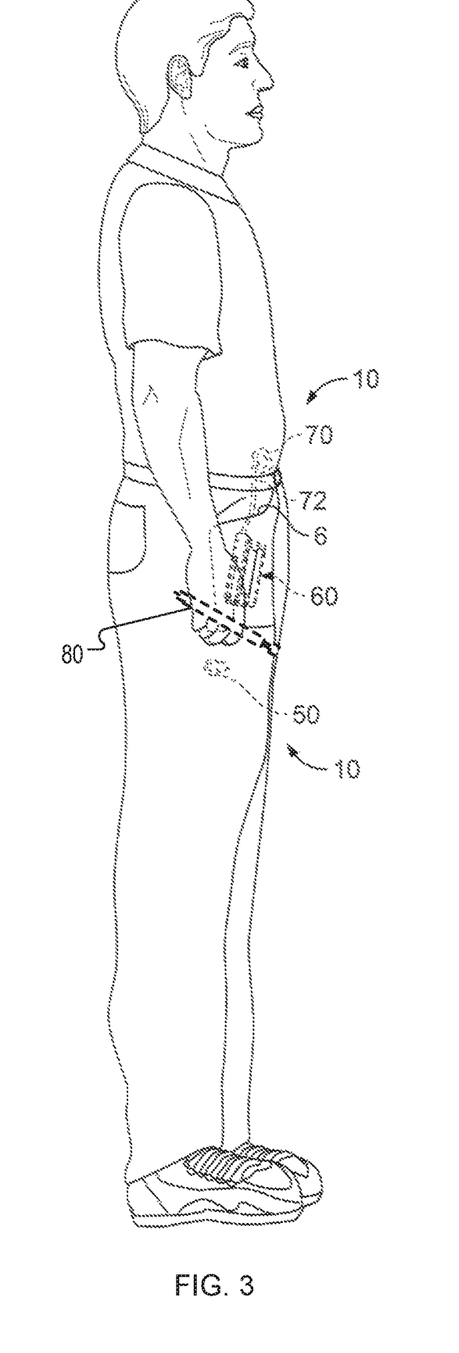
FIG. 3 is a perspective view of the infusion pump system of FIG. 2 in which the pump assembly is worn on clothing of a user, in accordance with particular embodiments.
Figure 4:
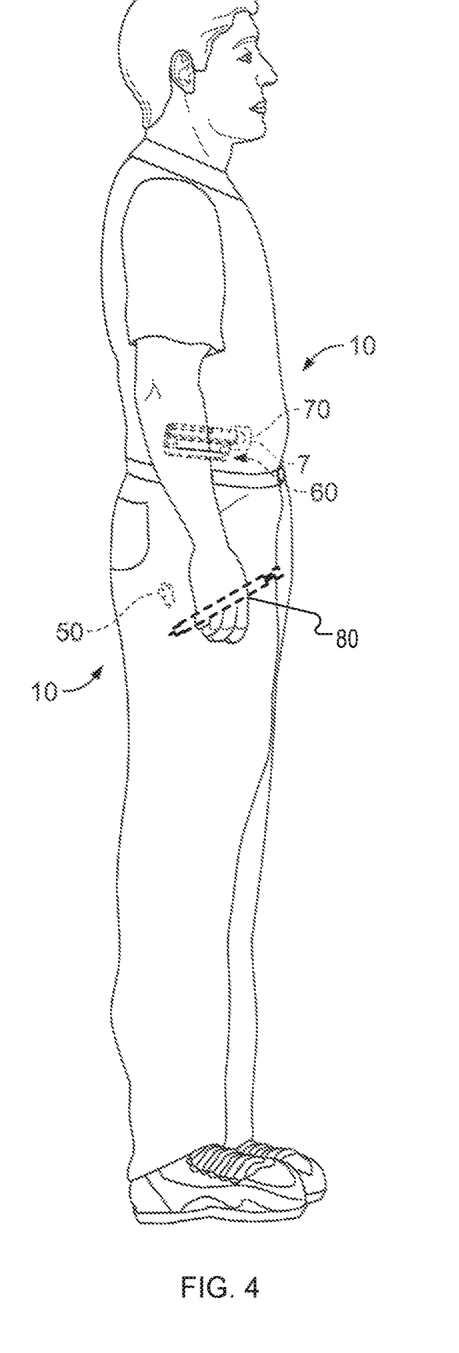
FIG. 4 is a perspective view of an infusion pump system of FIG. 2 in which the pump assembly is worn on skin of a user, in accordance with other embodiments.

Referring now to FIGS. 2-4, the pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (not shown in FIG. 2) that advances a plunger 125 in the fluid cartridge 120 so as to dispense fluid therefrom. In this embodiment, the drive system housed within the pump device 100 can include a battery-powered actuator, such as a rotational motor (not shown in FIG. 2), that acts upon a gear system to cause incremental adjustment of a ratchet mechanism to incrementally advance a piston rod engaged with the plunger 125. In some embodiments, the dispensed fluid exits the fluid cartridge 120, passes through a flexible tube 72 (FIG. 3) of an infusion set 70. The dispensed fluid can enter through the skin via a cannula of the infusion set 70.

In some embodiments, the controller device 200 communicates with the pump device 100 to control the operation of the pump drive system. When the controller device 200, the pump device 100 (including the cap device 130 in this embodiment), and the fluid cartridge 120 are assembled together, the user may conveniently wear the infusion pump system 60 on the user's skin under clothing or in the user's pocket while receiving the fluid dispensed from the pump device 100 (refer, for example, to FIGS. 3-4). Thus, in some embodiments, the pump assembly can operate as a portable unit that provides reliable delivery of insulin, glucagon, or another medication in a discrete manner.

The controller device 200 may be configured as a reusable component that provides electronics and a user interface 220 to control the operation of the pump device 100. In such circumstances, the pump device 100 can be a disposable component that configured and constructed to be discarded after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump system 60 can provide enhanced user safety as a new pump device 100 (and drive system therein) is employed with each new fluid cartridge 120.

Briefly, in use, the pump device 100 can be configured to removably attach to the controller device 200 in a manner that provides a secure fitting, an overall compact size, and a reliable electrical connection. The compact size permits the infusion pump system 60 to be discrete and portable. The controller device 200 of the infusion pump system can be used to provide glucose alarms indicative of high and low blood glucose levels (when compared to predetermined high and low blood glucose alarm levels, respectively), to provide glucose alarms indicative of rapidly increasing or decreasing blood glucose levels, and to modify predetermined high and low blood glucose alarm levels based on the rate at which a user's blood glucose level is changing.

It should be understood that, in alternative embodiments, the pump device 100 and the controller device 200 can be configured as a single housing unit in which the control components and the pump drive system are arranged in a single housing. In these alternative embodiments, the pump assembly (including the controller device and the pump device) may have a different size and shape and may operate as a reusable unit that can communicate with a number of monitoring devices (such as a blood glucose level monitoring device) over a period of time.

Still referring to FIGS. 2-4, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin, glucagon, or another medicine for use in the treatment of Diabetes (e.g., Byetta®, Symlin®, or others). Such a cartridge 120 may be supplied, for example, by Eli Lilly and Co. of Indianapolis, Ind. In some circumstances, the user may receive a scheduled, substantially continuous, basal rate of medicine from the fluid cartridge 120. In addition, or in the alternative, the user may receive intermittent, relatively larger, bolus dosages of medicine based on certain information. For example, the infusion pump system 60 can be used to supply a bolus dosage of insulin based on one or more meals recently entered into the controller device 200, previously received insulin, information specific to the user (e.g., insulin sensitivity), activity level, and information derived from data indicative of the user's blood glucose level. It should be understood from the description herein that the fluid cartridge 120 may have a configuration other than that depicted in FIG. 2. For example, the fluid cartridge may have a different outer shape or a different reservoir volume. In another example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more structures 119 that at least partially extend into the cavity 116 to engage a portion of the medicine cartridge 120 when the medicine cartridge 120 is installed therein. In this embodiment, the pump housing structure 110 includes a penetration barb 119 extending from to the piston rod of the pump device 110 so as to penetrate and fixed to the plunger 125 of the cartridge 120. After the medicine cartridge is inserted to a particular depth, the barb structure 119 irreversibly engages into the plunger 125 so that the medicine cartridge 120 remains inside the cavity 116. This engagement with the barb 119 and the plunger 125 hinders any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the barb structure 119 can interfere with attempts to remove the medicine cartridge 120 from the pump device 100, the pump device 100 will be discarded along with the medicine cartridge 120 after the medicine cartridge 120 is emptied, expired, or otherwise exhausted. The barb structure 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIG. 2, the cap device 130 can be joined with the pump device 100 after the medicine cartridge is at least partially inserted in the cavity 116. As shown in FIGS. 2-3, the cap device 130 may include an output port 139 (FIG. 2) that connects with the tubing 72 (FIG. 3) for dispensation of the medicine to the user. The output port 139 can be configured to mate with, or can be preassembled together with, the tubing 72 of the infusion set 70 (FIG. 3).

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the fluid cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

The controller device 200 may be configured to removably attach to the pump device 100, for example, in a side-by-side arrangement. The compact size permits the infusion pump system 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection. For example, the pump device 100 can include a channel 112 defined along the exterior of the housing 110 and a latch 114. The channel 112 can slidably mate with a corresponding rail structure (not shown in FIG. 2) along the housing 210 of the controller device 200. Also, the latch 114 can releasably lock with a corresponding tooth (not shown in FIG. 2) of the controller device 200. Such mating features of the pump housing structure 110 and the controller housing structure 210 can provide a secure, releasable connection when the controller device 200 is attached to the pump device 100

As shown in FIG. 2, the pump device 100 may include an electrical connector 118 (e.g., having conductive pads, pins, or the like) that are exposed to the controller device 200 and that mate with a complementary electrical connector on the adjacent face of the controller device 200. The electrical connectors provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump system 60 may include a gasket that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump system 60).

The controller device 200 includes the user interface 220 that permits a user to monitor the operation of the pump device 100. In some embodiments, the user interface 220 includes a display 222 and one or more user-selectable buttons (e.g., four buttons 224 in this embodiment). In addition to (or as an alternative to) the buttons 224, the display 222 of the user interface 220 can be equipped with a touchscreen configured to receive user input. The display 222 may include an active area in which numerals, text, symbols, images, or a combination thereof can be displayed. For example, the display 222 may be used to communicate a number of status indicators, alarms, settings, and/or menu options for the pump system 60. In some embodiments, the display 222 can inform the user of the amount of a suggested glucagon dosage, the user's blood glucose level, an indication that the user's blood glucose level is rising or falling, an indication that the user's blood glucose level is below a target level or range, an indication that the glucagon dosage suggestion includes a correction for the rate of change in the user's blood glucose level, and the like. In the example depicted in FIG. 2, the display 222 indicates a suggested glucagon amount of 0.8 mg. The display 222 also indicates that the user can accept the suggested glucagon amount by activating the left button 224 or decline it by activating the right button 224.

In some embodiments, the user may press one or more of the buttons 224 to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224 of the user interface 220. For example, in embodiments of the pump system 60 configured to dispense glucagon, the user may press one or more of the buttons 224 to change the dispensation rate of glucagon or to request that a bolus of glucagon be dispensed immediately or at a scheduled, later time. In another example, the user may use the buttons 224 to manually input information such as the user's current blood glucose level (e.g., as measured by an external blood glucose meter), the current rate of change in the user's blood glucose level, or the like into the pump system 60.

The display 222 of the user interface 220 may be configured to display information when no buttons 224 have been pressed. For example, as shown in FIG. 2, the active area of the display 222 can display a suggested glucagon dosage calculated by the controller device 200 and an indication that the glucagon dosage suggested includes a blood glucose rate of change correction. The display 222 can also display the user's blood glucose level (50 mg/dl in this example) and an indication of whether the user's blood glucose level is rising or falling (the downward facing arrow indicates a falling glucose level in this example). In addition to this information, the user interface may prompt the user to accept or decline the glucagon dosage suggestion (e.g., by pressing the left button 224 or the right button 224, respectively) or to enter a modified glucagon dosage amount. This information can be displayed until one of the buttons 224 has been actuated. This, or other, information can also be displayed for a period of time after no button 224 has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224 has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224 has been actuated (e.g., after 15 seconds or the like), and then the display 222 can enter sleep mode and become blank after a second period of time in which no button 224 has been actuated (e.g., after 30 seconds or the like). Thus, the dimming of the display device 222 can alert a user viewing the display device 222 when the active area of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto). Moreover, information related to the last delivered bolus can be displayed contemporaneously with the detected blood glucose value and an indication of whether the user's blood glucose level is rising or falling, so the user is provided with the opportunity to make informed decisions regarding the current and future status of his or her blood glucose level.

Also, in some embodiments described herein, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIG. 2. For example, in some embodiments, the user interface 220 may include only one button or may include a greater numbers of buttons, such as two buttons, three buttons, four buttons, more than four buttons, a full QWERTY keyboard, or the like. In another example, the user interface 220 of the controller device 200 may include a touch-sensitive screen so that a user may select buttons defined by the active area of the touch screen display. Alternatively, the user interface 220 may comprise audio inputs or outputs so that a user can monitor (e.g., through audio coming from the user interface 220) and/or modify (e.g., through voice commands) the operation of the pump device 100.

Referring to FIGS. 3-4, an infusion pump system 10 that includes the pump system 60 of FIG. 2 may be configured to be portable and can be wearable and concealable. For example, a user can conveniently wear the infusion pump system 60 on the user's skin (e.g., skin adhesive) underneath the user's clothing or carry the pump system 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, and about 5 cm to about 7 cm in this embodiment, the overall length of the pump housing structure 110 (which contains medicine cartridge and the drive system) can be about 10 cm or less, and about 6 cm to about 9 cm in this embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump system 60 (including the removable controller device 200 attached to the pump device 100 having the cap 130) may have an overall length of about 11 cm or less, and about 7 cm to about 10 cm in this embodiment; an overall height of about 6 cm or less, and about 2 cm to about 5 cm in this embodiment; and an overall thickness of about 20 mm or less, and about 8 mm to about 20 mm in this embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the user's subcutaneous tissue or vasculature). The infusion set 70 may include the flexible tube 72 that extends from the pump device 100 to a subcutaneous cannula retained by a skin adhesive patch that secures the subcutaneous cannula to the infusion site.

Referring to FIG. 3, in some embodiments, the infusion pump system 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump system 60 and use the tube 72 of the infusion set 70 to direct the dispensed medicine to the desired infusion site. In some circumstances, the user may desire to wear the pump system 60 in a more discrete manner. Accordingly, the user may pass the tube 72 from the pocket 6, under the user's clothing, and to the infusion site. As such, the pump system 10 can be used to deliver medicine to the tissues or vasculature of the user in a portable, concealable, and discrete manner. Furthermore, a monitoring device 50 (such as a blood glucose monitoring device) can be worn on the user's skin while the pump system 60 is carried by the user (e.g., in a pocket). As such, the monitoring device 50 can communicate information indicative of the user's blood glucose level to the pump system 60 while the pump system 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump system 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump system 60 is worn on the user's skin in a different location from that where the monitoring device is worn. As such, the monitoring device 50 can communicate information indicative of the user's blood glucose level to the pump system 60 while the pump system 60 is used to deliver medicine through the infusion set 70. In this embodiment, the monitoring device 50 may be arranged on the user's skin at a location that is spaced apart from the infusion set 70.

Figure 5:
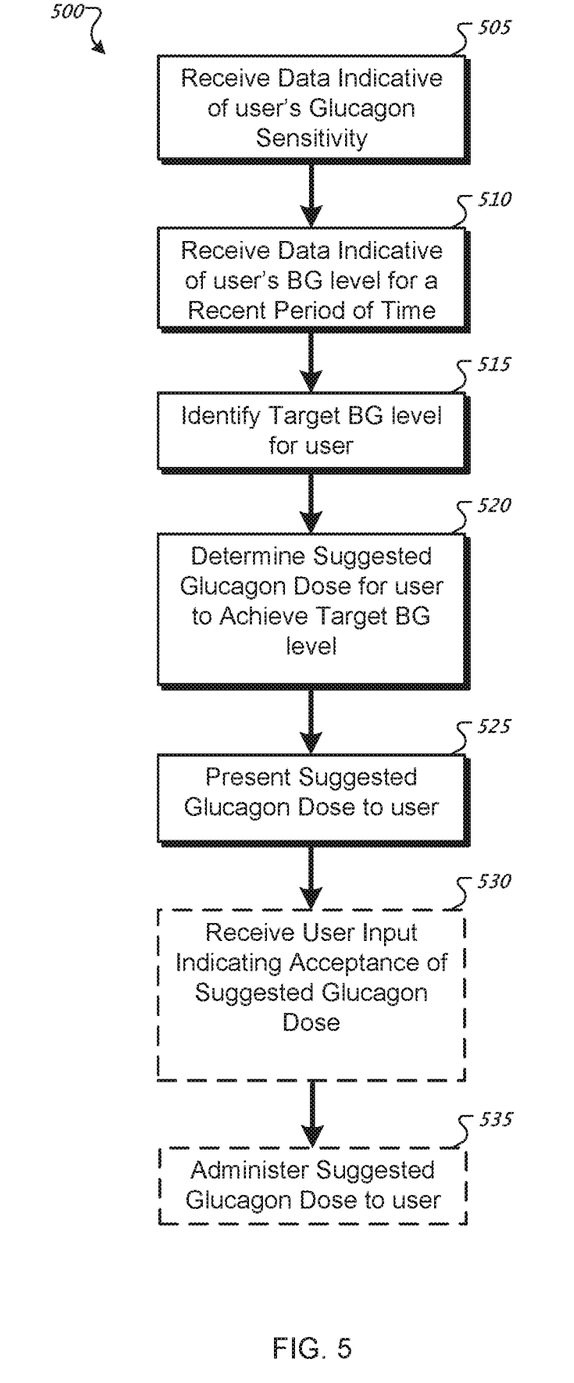
FIG. 5 is a flow diagram depicting an exemplary process of determining and suggesting a glucagon dose for a user.

Referring now to FIG. 5, an illustrative process 500 for determining a suggested glucagon dosage (and optionally administering that suggested glucagon dosage), can include a number of operations performed by the controller device 200 of the infusion pump system 60 (or by the controller 62 described in connection with FIG. 1). The process 500 can also be performed by one or more other devices other than the controller device 200 or the infusion pump system 60. For example, some or all of the operations included in the process 500 can be performed by a mobile phone, a tablet device, a personal computer, control circuitry included as part of a blood glucose monitor, or control circuitry attached to or in communication with a glucagon injector pen.

In operation 505, the controller device 200 can receive data indicative of a user's glucagon sensitivity. For example, the user can use controls 224 of the controller device 200 to enter the user's glucagon sensitivity value into the controller device 200. In some circumstances, the user's glucagon sensitivity value can be a clinically determined value (determined at a clinic or determined based upon the user's previous dosage history data), which is manually input to the controller device via the user interface 220 and stored in a memory device of the controller device 200. As another example, the controller device 200 can receive an indication of the user's glucagon sensitivity via a wired or wireless connection with a remote device, such as a mobile phone or tablet device. As yet another example, a user can enter a glucagon sensitivity value into a device (such as a mobile phone) using a touch screen of the device.

In operation 510, the controller device 200 can receive data indicative of a user's blood glucose level for a recent period of time, including a most recent blood glucose measurement. For example, the controller device 200 can retrieve 1 to 3 blood glucose level values, representing the information for the 1 to 3 most recent blood measurements, from memory. In another example, the controller device 200 can retrieve one or more recent blood glucose levels stored in memory and can initiate a current blood glucose measurement (e.g., by receiving information from the glucose monitoring device 50, by instructing the user to perform a blood glucose measurement and input the data into the controller device 200, by inserting a glucose test strip containing a blood sample into a strip reader device that communicates with the controller device 200, or the like). In yet another example, the controller device 200 can retrieve blood glucose information for a period of time (e.g., less than one hour, less than 30 minutes, about 2 minutes to about 20 minutes, and about 5 minutes to about 15 minutes) for use in the calculation of the blood glucose correction component.

In some embodiments, additional information can be received. For example, the controller device 200 can receive food on board (FOB) data and insulin load data. FOB is a measurement of food previously consumed by a user. In one embodiment, FOB is a measurement of food that has been consumed by a user, but not yet converted into glucose usable by the body for metabolism. The insulin load data can be in the form of insulin-on-board (IOB) or total insulin load (TIL), as previously described. In some embodiments, additional information that can be received by the controller device 200 can include an indication of glucagon on board (GOB). For example, the controller device 200 can access memory to identify a previous amount of glucagon administered to a patient, as well as a time duration since the glucagon was administered. As another example, a glucagon administration device (such as a glucagon pen) can provide GOB information (e.g., through a wireless or wired communication link) to the controller device 200. The GOB information can include one or more dosage amounts of glucagon, time since the glucagon was administered, and/or time at which the glucagon was administered.

In various embodiments, the controller device 200 may use the FOB and/or insulin load information in combination with blood glucose level information and glucagon sensitivity value for the user to calculate a suggested glucagon dosage amount. In various embodiments, individual parameters such as sensitivity to insulin, sensitivity to glucagon, sensitivity to carbohydrates or other endocrine information may allow the pump to improve the accuracy of suggested glucagon dosages.

An onboard assistance system may include a processing method, for example, which incorporates carbohydrate, protein, and fat values to determine a value for food on board ("FOB") for the user. The FOB calculation might correspond to the equivalent amount of carbohydrate for each of the protein and fat intakes. As such, the pump user may request a task, and be given further assistance by the onboard assistance system to carry out the task with accuracy.

The onboard assistance program may include a monitoring method that incorporates previously entered data and treatment information to determine a value for IOB for the user. In general, an IOB feature in a pump calculates the decay of insulin in the body after a bolus of insulin is given to a pump user. The infusion pump system may recognize current dosage levels that a user is receiving and further, can measure the dosage to determine future infusion dosages or rates. The pump user can input several variables that the pump system can utilize to recommend one or more treatments (such as, for example, administration of a dosage of glucagon). Advantageously, using an infusion pump having manual and autonomous control properties may allow an accurate estimate of a particular bolus rate or amount.

Other information that can be received by the controller device 200 (or another device performing some or all of the operations of the process 500) include of total insulin load (TIL) for the user and an activity level for the user. A TIL value can correspond to an insulin load calculation that includes previous basal and bolus dosages of insulin, previously consumed food, previously administered glucagon, or the like. Activity level can be a user specific, time sensitive function that includes quantified activity levels represented by a time based decay function that assumes activity has a near term effect of significantly lowering glucose during a short term period, as well as a long term effect of lowering glucose to a lesser degree for an extended time period. For example, the decay function can be based on an assumption that a given activity would have a near term effect of significantly lowering blood glucose of a user within an hour or less of the activity as well as a long term effect of lowering blood glucose of the user to a lesser degree over a period of 4 to 8 hours.

In some embodiments, the process 500 can include calculating the blood glucose rate of change for the most recent time. For example, the controller device 200 can subtract the blood glucose level corresponding to a previous measurement from the most recent measurement and divide this value by the change in time between the two measurements. In another example, three or more recent blood glucose measurements can be used to provide a broader range of data points for the calculated rate-of-change parameter (e.g., in an effort to reduce the effect of any noise in the signal from the glucose monitoring device 50) or to also produce the acceleration of the glucose. In another example, the controller device 200 can estimate the instantaneous blood glucose rate of change at a time (e.g., the most current measurement) from a blood glucose curve.

After receiving data indicative of one or more parameters associated with the user, the process 500 can execute operation 515 of identifying a target blood glucose level for the user. The target blood glucose level can be a value (e.g., 90 mg/dL) or a value range (e.g., 80 to 100 mg/dL) and the target may vary over the course of the day or day of the week or month. In some implementations, the target blood glucose level can be identified, based in part on a weight or age of the user or other user condition such as pregnancy or hypoglycemia unawareness. The target blood glucose level can be stored in a memory accessible by the controller device 200. The controller device 200 can access the memory to identify the target blood glucose level for the user.

The controller device 200 can compare the identified target blood glucose level for the user and information indicative of the user's current blood glucose level to determine that the user's blood glucose level is below the target level.

At operation 520, the process 500 can determine a suggested glucagon dose for the user to achieve the identified target blood glucose level. In some embodiments, the operation 520 can be performed in response to a determination that the user's blood glucose level is below the target level. The suggested glucagon dose can be displayed to the user to cause the user to administer glucagon to achieve a blood glucose level that is proximate to the target level (or is within the target level range). If the target blood glucose level is a range, the suggested glucagon dose can be determined to cause the user's blood glucose level to reach the bottom value of the range, to reach a mid-point value of the range, or to reach another specified value within the range (for example, a suggested glucagon dose can be calculated to cause the user's blood glucose level to at least exceed a value that is 5 mg/dL greater than the bottom of the target blood glucose range). The controller device 200 can use various parameters associated with the user to determine the suggested glucagon dose for the user. For example, the controller device 200 can use the user's current blood glucose level, the target blood glucose level, and the user's glucagon sensitivity value to determine a suggested glucagon dose according to the following formula:

Suggested Glucagon Dose=(Target BG−Current BG)/
Glucagon Sensitivity

Stepping through the above equation, if, for example, the user's current BG level is 50 mg/dL, the user's target BG level is 90 mg/dL, and the user's glucagon sensitivity is 20 mg/dL/Unit of Glucagon, then the above equation would be solved as:

Suggested Glucagon Dose=(90−50)/20=40/20=2
Units of Glucagon

Depending upon the concentration of the glucagon fluid, a "Unit" of glucagon correlates to a particular number of milligrams (mg) or micrograms (mcg) of Glucagon. For example, in this embodiment, a "Unit" of glucagon correlates to 0.4 mg of glucagon, so the suggested glucagon dose of 2 Units of glucagon would be 0.8 mg of glucagon (refer to the screen display in FIG. 2).

In some embodiments, rather than a current BG level for the user, a projected BG level for the user can be identified based on a determined BG level rate of change for the user and a previously identified BG level for the user. The controller device 200 can then use the projected BG level to determine a suggested glucagon dose according to the following formula:

Suggested Glucagon Dose=(Target BG−Projected
BG)/Glucagon Sensitivity

As described above, additional parameters can also be used when determining a suggested glucagon dosage to achieve a target BG level for the user. For example Insulin on Board (IOB) or Total Insulin Load (TIL) values can be used in combination with an insulin sensitivity for the user when determining a suggested glucagon dose. For example, IOB can be used to determine a suggested glucagon dose for the user according to the formula:

Suggested Glucagon Dose=(Target BG−Current BG−
(IOB/Insulin Sensitivity))/Glucagon Sensitivity Similarly, TIL can be used to determine a suggested glucagon dose for the user according to the formula:

Suggested Glucagon Dose=(Target BG−Current BG−
(TIL/Insulin Sensitivity))/Glucagon Sensitivity Another factor that can be considered when determining the suggested glucagon dose is a recent activity of the user. The effect of an activity on a user can be quantified as an activity level divided by an activity sensitivity for the user (where the activity sensitivity defines how the user's BG level changes in response to activity). Activity level can be used to determine a suggested glucagon dose for the user according to the formula:

Suggested Glucagon Dose=(Target BG−Current BG−
(Activity Level/Activity Sensitivity))/Glucagon
Sensitivity Yet another parameter that can be taken into consideration when determining the suggested glucagon dose for the user is Food on Board (FOB). For example, the FOB value can indicate a number of grams of carbohydrates ingested by the user. This value can be utilized along with a "carb ratio" for the user (i.e., a ratio indicating effect of carbohydrates on the BG level of the user). FOB can be a time sensitive function where food action is assumed to decay over a period of time from the time of ingestion. Food action may vary based on the content of the food, with protean and fat components having a longer time function in comparison to high glycemic index carbohydrates, which have a very short time function and low glycemic index carbohydrates, which have a moderate time function. FOB can be used to determine a suggested glucagon dose for the user according to the formula:

Suggested Glucagon Dose=(Target BG−Current BG+
(FOB/Carb Ratio))/Glucagon Sensitivity Another parameter that can be taken into consideration when calculating a suggested glucagon dose is glucagon on board (GOB). The GOB value can be, for example, received from a glucagon administration device, or be entered into a suggested glucagon dose calculator manually by a user. The GOB can be, for example, a measure of the amount of glucagon in a user's system that has not yet been processed. GOB can be used to determine a suggested glucagon dose for the user according to the formula:

Suggested Glucagon Dose=(Target BG−Current BG)/
Glucagon Sensitivity−GOB

It should be understood from the teachings herein that, in some embodiments, any combination of the aforementioned parameters can be taken into consideration by the glucagon dosage calculator when calculating a suggested glucagon dose. For example, in particular embodiments, all of these aforementioned parameters can be taken into account when calculating a suggested glucagon dose:

Suggested Glucagon Dose=[Target BG−Current BG−
(IOB/Insulin Sensitivity)−(Activity Level/Activity Sensitivity)+(FOB/Carb Ratio)]/Glucagon
Sensitivity—GOB (Note that TIL can be implemented instead of IOB.)

Other combinations of the above discussed parameters can be used when determining a suggested glucagon dose for the user. Additional parameters could also be used in determining a suggested blood glucagon dose for the user.

Still referring to the embodiment in FIG. 5, after determining the suggested glucagon dose for the user, the process 500 can execute operation 525 and present the suggested glucagon dose to the user. For example, the suggested glucagon dose can be displayed on the user interface 220 of the infusion pump system 60. As another example, voice synthesis circuitry of an infusion pump assembly in combination with one or more speakers can be used to audibly indicate the suggested blood glucagon dose to the user. As yet another example, the suggested blood glucagon dose can be displayed on the display screen of a mobile phone, computer, blood glucose monitor, or a tablet device. The suggested glucagon dose could also be displayed on a display screen attached to or in communication with a glucagon pen or other glucagon delivery device.

In some embodiments, the suggested glucagon dose is transmitted from a first device to a second device for presentation to the user. For example, the operations 405-420 can be performed by the controller device 200 of the infusion pump system 60. The suggested glucagon dose can then be transmitted to the user's mobile phone for presentation to the user (e.g., through a Bluetooth connection, or via an SMS message). As another example, the suggested glucagon dose can be determined by circuitry included as part of a blood glucose monitor and transmitted to a user's tablet device for presentation to the user.

The process 500 can execute an optional operation 530 by receiving user input indicating acceptance of the suggested glucagon dose. For example, the suggested glucagon dose can be displayed on the user interface 220 of the controller device 200. The user can use the buttons 224 to accept or decline the suggested glucagon dose. As another example, voice recognition capability of the controller device 200 can be used to allow the user to verbally accept the suggested glucagon dosage. In some embodiments, the user can manually modify the suggested glucagon dosage.

The process 500 can further execute an optional operation 535 by administering a suggested glucagon dose to the user. For example, the controller device 200 can, in response to receiving an acceptance of the suggested glucagon dose, send control signals to the disposable pump device 100 to cause the disposable pump device 100 to administer the suggested glucagon dose to the user. As another example, the suggested glucagon dose can be presented to the user on the user's mobile phone. The user can then accept the suggested glucagon dose, and an indication of the suggested glucagon dose can be transmitted to a glucagon delivery device (such as an infusion pump) to cause the glucagon delivery device to administer the suggested glucagon dose to the user. In some embodiments, the user can manually administer the suggested glucagon dose using a syringe, glucagon pen, or other glucagon delivery device. For example, the user can use a mobile application installed on the user's mobile phone to determine a suggested glucagon dose. The application can display the suggested glucagon dose to the user on a display screen of the mobile phone. The user can then use a glucagon pen to administer the suggested glucagon dose.

A number of embodiments of the invention have been described. Nevertheless, it will be understood that various modifications may be made without departing from the spirit and scope of the invention. Accordingly, other embodiments are within the scope of the following claims.

What is claimed is:

1. A medicine administration system, comprising:
   a wearable glucose monitoring device;
   a disposable and non-reusable insulin delivery device including:
     an insulin cartridge comprising a plunger, a septum, and insulin;
     a housing that retains the insulin cartridge; and
     a drive system comprising a piston rod that is incrementally movable to apply a dispensing force to the plunger to dispense insulin through the septum;
   a removable controller device including:
     a controller housing that is removably attachable to the housing of the insulin delivery device;
     a user interface comprising a display and one or more user-selectable buttons; and
     a wireless communication device to receive glucose information from the wearable glucose monitoring device, the glucose information being indicative of a blood glucose level of the user,
     wherein the removable controller device displays a suggested glucagon dosage in response to user input to the system, the suggested glucagon dosage being at least partially dependent upon a glucose sensitivity value, a target blood glucose level, and the blood glucose level of the user; and
   a glucagon injector pen device or syringe that is separate from the disposable and non-reusable insulin delivery device and the controller device.

2. The system of claim 1, wherein the controller device is configured to activate a glucagon dosage calculator that calculates the suggested glucagon dosage based at least in part on the glucose sensitivity value stored by the controller device, the target blood glucose level stored by the controller device, and the blood glucose level of the user.

3. The system of claim 1, wherein the glucagon injector pen device or syringe is a glucagon injector pen in wireless communication with the removable controller device.

4. The system of claim 1, further comprising:
   a computer-readable program executed on a smart phone or tablet device, wherein the suggested glucagon dosage is calculated by the computer-readable program.

5. A medicine administration system, comprising:
   a wearable glucose monitoring device;
   a disposable and non-reusable insulin delivery device including:
     an insulin cartridge comprising a plunger, a septum, and insulin;
     a housing that retains the insulin cartridge; and
     a drive system comprising a piston rod that is incrementally movable to apply a dispensing force to the plunger to dispense insulin through the septum;
   a removable controller device including:
     a controller housing that is removably attachable to the housing of the insulin delivery device;
     a user interface comprising a display and one or more user-selectable buttons; and
     a wireless communication device to receive glucose information from the wearable glucose monitoring device, the glucose information being indicative of a blood glucose level of the user; and
   a glucagon dosage suggestion calculator that calculates a suggested glucagon dosage being at least partially dependent upon a glucose sensitivity value, a target blood glucose level, and the blood glucose level of the user; and
   a glucagon injector pen device or syringe that is separate from the disposable and non-reusable insulin delivery device and the controller device.

6. The system of claim 5, wherein the glucagon dosage suggestion calculator comprises a computer readable program executed on a smart phone or tablet device.

7. The system of claim 5, wherein the glucagon dosage calculator is attached to the glucagon injector pen device or syringe.

8. The system of claim 5, wherein the glucagon dosage suggestion calculator is configured to interact with the glucagon injector pen device or syringe.

9. The system of claim 5, wherein the glucagon injector pen device or syringe is a glucagon injector pen in wireless communication with the removable controller device.

10. The system of claim 5, wherein the disposable and non-reusable insulin delivery device is an insulin pump.

\* \* \* \* \*